(12) United States Patent
Tinni et al.

(10) Patent No.: US 10,359,379 B2
(45) Date of Patent: Jul. 23, 2019

(54) METHODS OF DETERMINING SHALE PORE CONNECTIVITY

(71) Applicant: The Board of Regents of the University of Oklahoma, Norman, OK (US)

(72) Inventors: Ali Ousseini Tinni, Norman, OK (US); Carl Sondergeld, Norman, OK (US); Chandra Rai, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 68 days.

(21) Appl. No.: 15/631,269

(22) Filed: Jun. 23, 2017

(65) Prior Publication Data

US 2018/0003653 A1 Jan. 4, 2018

Related U.S. Application Data

(60) Provisional application No. 62/354,484, filed on Jun. 24, 2016.

(51) Int. Cl.
*G01N 24/08* (2006.01)
*G01N 15/08* (2006.01)
*G01R 33/44* (2006.01)

(52) U.S. Cl.
CPC ........... *G01N 24/081* (2013.01); *G01N 15/08* (2013.01); *G01R 33/448* (2013.01)

(58) Field of Classification Search
CPC ............................ G01N 24/081; G01R 33/448
USPC ........................................................ 324/309
See application file for complete search history.

(56) References Cited

U.S. PATENT DOCUMENTS

| 7,893,692 B2 * | 2/2011 | Minh ..................... G01V 3/32 |
| | | 324/303 |
| 9,423,365 B2 * | 8/2016 | Nicot ..................... G01V 3/32 |
| 9,720,124 B2 * | 8/2017 | Kadayam Viswanathan .............. |
| | | G01V 3/32 |

OTHER PUBLICATIONS

Luffel, D.L., et al.; "Matrix Permeability Measurement of Gas Productive Shales"; Society of Petroleum Engineers; SPE 26633 (1993) 10 pages.
Bailey, S; "Closure and Compressibility Corrections to Capillary Pressure Data in Shales"; Colorado School of Mines, DWLS 2009 Fall Workshop, Beyond the Basics of Capillary Pressure: Advanced Topics and Emerging Applications; Oct. 19, 2009; 38 pages.
Kale, S.; "Petrophysical Characterization of Barnett Shale Play"; University of Oklahoma (2009) 130 pages.
Sisk, C., et al.; "3D Visualization and Classification of Pore Structure and Pore Filling in Gas Shales"; Society of Petroleum Engineers; SPE 134582 (2010) 4 pages.
Curtis, M.E., et al.; "Investigating the Microstructure of Gas Shales by FIB/SEM Tomography & STEM Imaging"; University of Oklahoma; SPE 144391 (2011) 28 pages.

(Continued)

*Primary Examiner* — Reena Aurora
(74) *Attorney, Agent, or Firm* — Hall Estill Law Firm

(57) ABSTRACT

A method of using NMR to estimate pore connectivity in a shale formation by estimating organic pore connectivity in a first sample of the shale formation and inorganic pore connectivity in a second sample of the shale formation based on uptake of brine and hydrocarbon phases. Porosity partitioning of the shale formation may be estimated with a third sample of the shale formation.

7 Claims, 19 Drawing Sheets

(a)

(b)

(56) References Cited

OTHER PUBLICATIONS

Handwerger, D.A., et al.; "Improved Petrophysical Core Measurements on Tight Shale Reservoirs Using Retort and Crushed Samples"; Society of Petroleum Engineers; SPE 147456 (2011) 21 pages.
Odusina, E.; "An NMR Study on Shale Wettability"; University of Oklahoma (2011) 111 pages.
Tinni, Ali, et al.; "Shale Permeability Measurements on Plugs and Crushed Samples"; Society of Petroleum Engineers; SPE 162235 (2012) 28 pages.
Sulucarnain, I.; "An NMR Study of Shale Wettability and Effective Surface Relaxivity"; University of Oklahoma (2013) 115 pages.
Dang, S.T., et al.; "A New Approach to Measure Organic Density"; Unconventional Resources Technology Conference; URTeC: 1921752 (2014) 7 pages.
Hu, Q., et al.; "Pore Accessibility and Connectivity of Mineral and Kerogen Phases in Shales"; Unconventional Resources Technology Conference; URTeC: 1922943 (2014) 17 pages.
Peng, S., et al.; "Upscaling of Pore Network and Permeability from Micron to Millimeter Scale in Organic-Pore Dominated Mudstones"; Search and Discovery; Article #41429 (2014) 31 pages.
Xu, M., et al.; "Advances in Understanding Wettability of Gas Shales"; American Chemical Society; Energy & Fuels (2014) 4362-4375.
King, H.E., Jr., et al.; "Pore Architecture and Connectivity in Gas Shale"; American Chemical Society; Energy & Fuels (2015) 1375-1390.
Klaver, J., et al.; "The connectivity of pore space in mudstones: insights from high-pressure Wood's metal injection, BIB-SEM imaging, and mercury intrusion porosimetry"; Geofluids (2015) 15, 577-591.

\* cited by examiner

METHODS OF DETERMINING SHALE PORE CONNECTIVITY

CROSS-REFERENCE TO RELATED APPLICATIONS

This application claims benefit under 35 U.S.C. 119(e) of U.S. Provisional Application Ser. No. 62/354,484, filed Jun. 24, 2016, which is hereby expressly incorporated herein by reference in its entirety.

STATEMENT REGARDING FEDERALLY SPONSORED RESEARCH OR DEVELOPMENT

Not applicable.

BACKGROUND

Production of natural gas from shale has become an important energy supply in the U.S. However, shale strata vary widely in the capacity to be exploited for gas production. One factor which affects the potential for gas recovery is the pore architecture, e.g., pore connectivity, of a particular shale reservoir. Shales are sedimentary rocks which contain both organic and inorganic matter and porosity and wettability vary widely. An ability to evaluate porosity is important to an understanding of a shale reservoir and how it can be exploited.

Current technologies used to evaluate pore connectivity in shales are based on (1) mercury intrusion and (2) permeability measurements. For mercury intrusion, the most popular instruments are the Micrometrics Autopore™ series. The Autopore™ instruments inject mercury in increasing pressure steps to measures the pore volume accessible through pore throats of different sizes. The dimensions of the pore throats can be calculated from the mercury intrusion pressures. However, in shale samples, pressures greater than 5000 psi (e.g., 10,000 psi) are required for mercury to enter the pore space. The high pressures required for mercury intrusion compress the shales and reduce the size of compliant pores. Therefore the results obtained after mercury intrusion cannot be used in reservoir evaluation.

Several systems for permeability measurements are available. During permeability measurements, a fluid (generally gas) is flowed through a porous sample, and the pressure and/or flow rate data is analyzed to obtain a permeability value. The PDP 250™ instrument is used by Core Lab (a major provider for oil field services) to measure permeability. However, due to the fissile nature of shales, permeability measurements are often dominated by fractures and do not represent flow in the shale matrix.

Pore connectivity measures how the pore system is connected throughout a volume of rock. It is a physical concept which is often thought to be measured by permeability or effective porosity in conventional reservoirs rocks. Shale permeability measurements are often affected by the presence of fractures which act as bypass conduits, and measurement of effective porosity has been an elusive concept in shales. The standard methods used to evaluate pore connectivity in conventional rocks are not applicable in shales. Several authors have used the combination of focused ion beam (FIB) and scanning electron microscopy (SEM) to build 3D volumes of several shale samples. From the 3D shale volumes, they extracted the connected and non-connected pore systems and studied the connectivity levels in the samples. However, the extraction of the pore spaces from 3D volumes relies on the establishment of subjective gray scales thresholds for the pore systems; hence the resultant pore spaces will be strongly dependent on the researcher. Mercury injection capillary pressure (MICP) was used to study pore connectivity in shales. It was reported that mercury starts to intrude the shale samples at pressures greater than 5,000 psi. This translates into pore throat diameters smaller than 36 nm. The MICP experiment provides a pore throat size distribution, but does not allow the investigation of how the pores are connected. In order to study which pores are connected and how they are connected Wood's metal was injected into in shale samples. Wood's metal is an alloy that melts at 70° C. Molten Wood's metal was injected in the shale samples at a maximum pressure of 87,000 psi and 46,000 psi. The smallest pore throats accessible at 87,000 psi and 46,000 psi were, respectively, equal to 2.3 nm and 4 nm. After the injection of Wood's metal, the samples were cooled to room temperature while maintaining the maximum pressures. This process solidified the Wood's metal, and the distribution of Wood's metal throughout the samples was studied with the SEM. Wood's metal penetrated essentially the pores at the edge of the samples, microfractures, and the vicinity of the microfractures. The concentration of Wood's metal in the middle of the samples was quantified as equal to approximately $\frac{1}{1000}^{th}$ of the concentration at the edges. Wood's metal and mercury are both non-wetting; hence a significant part of the mercury intrusion volumes recorded during MICP on shales did not enter the samples. The false intrusion reflects the compressibility of the shale sample.

Conventional methods fail to distinguish the different wettability systems contained in shale reservoirs. Therefore, new methods for determining pore connectivity and other pore characteristics of shale deposits are needed to improve the efficiency of shale gas production.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

DETAILED DESCRIPTION

Figure 1:
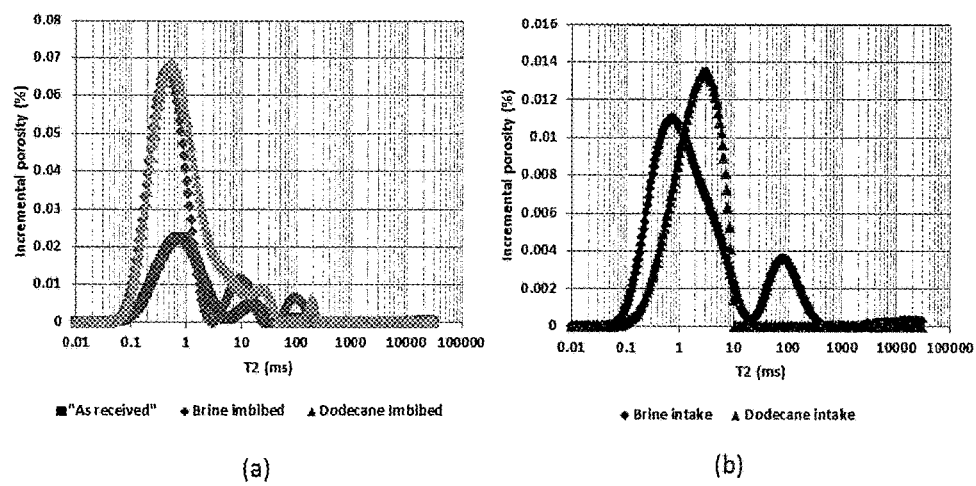
FIG. 1 shows NMR $T_2$ spectra acquired on a Barnett shale sample during a Sequence 1 treatment (a) and brine and dodecane intakes (b). To obtain the brine intake, the echo-train of the "As received" state was subtracted from the echo-train of the brine imbibed state. The dodecane intake was obtained by subtracting the echo-train of the brine imbibed state from the dodecane imbibed state. The echo-train generated after the subtractions is inverted to obtained NMR $T_2$ distribution in (b).

In at least one embodiment, the present disclosure is directed to a method of measuring shale pore connectivity and porosity partitioning between inorganic and organic material in a shale reservoir by using a combination of brine and hydrocarbon intrusion in shale samples as well as NMR measurements to determine the connectivity level and the porosity associated of the water wet and hydrocarbon wet pores networks. The method enables the classification of different geological facies of a formation based on their hydrocarbon delivery potential.

Before describing various embodiments of the present disclosure in more detail by way of exemplary description, examples, and results, it is to be understood that the present disclosure is not limited in application to the details of methods and compositions as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains.

All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used herein, the words "comprising" (and any form of comprising, such as "comprise" and "comprises"), "having" (and any form) of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error. Further, in this detailed description, each numerical value (e.g., temperature or time) should be read once as modified by the term "about" (unless already expressly so modified), and then read again as not so modified unless otherwise indicated in context. As noted, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

In certain embodiments of the present disclosure, the shale pore connectivity method is based on the suction of wetting fluids by pores with defined wettability. Shale reservoirs have porosity associated with organic matter, inorganic minerals and the interfaces between organic matters and inorganic minerals. The organic pores are defined herein as "hydrocarbon wet", the inorganic pores are defined herein as "water wet" and the pores at the interfaces between organic matter and inorganic minerals are defined herein as "mixed wet". Porosity, defined herein as the nonsolid or pore volume percentage or fraction of a rock sample, is a dimensionless volume ratio given herein as porosity units (p.u.), wherein 1 p.u.=1%. NMR $T_2$ is used to calculate porosities based on a calibration factor determined for deionized water by the following:

$$\text{porosity } (\phi) = (\text{Area under NMR spectrum}) \div [(\text{Number of scans}) \ast (\text{calibration factor}) \ast (\text{bulk volume})].$$

Shales have pores associated with the inorganic minerals, the organic matter and the combination of organic and inorganic interfaces. This observation implies the existence of three different wettability systems; a water wet system associated with the water wet inorganic minerals (clays, quartz and feldspars), a hydrocarbon wet system associated with the organic matter as well as the hydrocarbon wet minerals (carbonates), and the mixed wet system controlled by pores formed by the water wet and hydrocarbon wet components.

The presence of different wettability systems will affect significantly fluid distribution and its flow. For example, water can enter a clay pore at atmospheric pressure by simple capillary suction while oil can only enter a clay pore after the application of a pressure inversely proportional to the pore size (capillary pressure). However, both fluids can enter the mixed wettability pores at atmospheric pressure. Therefore, assessments of pore connectivity should take into account the existence of different wettability systems. Studies conducted with non-wetting fluids such as mercury and Wood's metal cannot provide a good understanding of how pores are connected in shales. The presence of water wet and hydrocarbon wet systems has been recognized during imbibition studies, but the connectivity levels in each system and how the different wettability systems interact has not been characterized prior to the work disclosed herein.

Experimental

Pore Connectivity at Atmospheric Pressure

Experimental Procedures and Sample Description

Pore connectivity at atmospheric pressure was investigated with brine (25,000 ppm KCl) and dodecane sequential imbibition at the Integrated Core Characterization Center of the University of Oklahoma. KCl brine and dodecane were used because of their respective affinities for water wet and hydrocarbon wet pores. Note that the presently disclosed methods are not limited to the use of KCl/water as a solvent to analyze water wet pores or to dodecane as a solvent to analyze hydrocarbon wet pores. For example, any suitable salt, such as NaCl can be used for the brine. Further, any suitable concentration of the solute can be used in the brine solution. Any suitable hydrocarbon solvent can be used for the liquid hydrocarbon phase. In at least certain embodiments, the hydrocarbon has a viscosity which is ≤ about 3 cP. The imbibition experiments were conducted on 45 shale samples obtained from Haynesville, Woodford, Barnett, Eagle Ford, Floyd, Utica-Collingwood and Wolfcamp formations. The samples from Haynesville, Barnett and Floyd were from the gas window. The samples from Utica-Collingwood were from the condensate window. The Eagle Ford samples were from the gas and condensate windows. The Wolfcamp samples were from the oil window.

Two imbibition sequences were performed on the "As received" samples. In a treatment designated as "Sequence 1" a sample was immersed in brine for 48 hours, followed by an immersion in dodecane for 48 hours. In a treatment designated as "Sequence 2" a sample was first immersed in dodecane for 48 hours, followed by an immersion in brine for 48 hours. Companion samples from the same depths as the samples used in Sequence 1 were used in Sequence 2.

After every immersion step, the amount of brine and dodecane imbibed was quantified by the acquisition of the NMR $T_2$ spectra of the samples. The NMR measurements were conducted at a TE of 300 μsec on Oxford Maran Ultra™ 2 MHz instruments.

Figure 2:
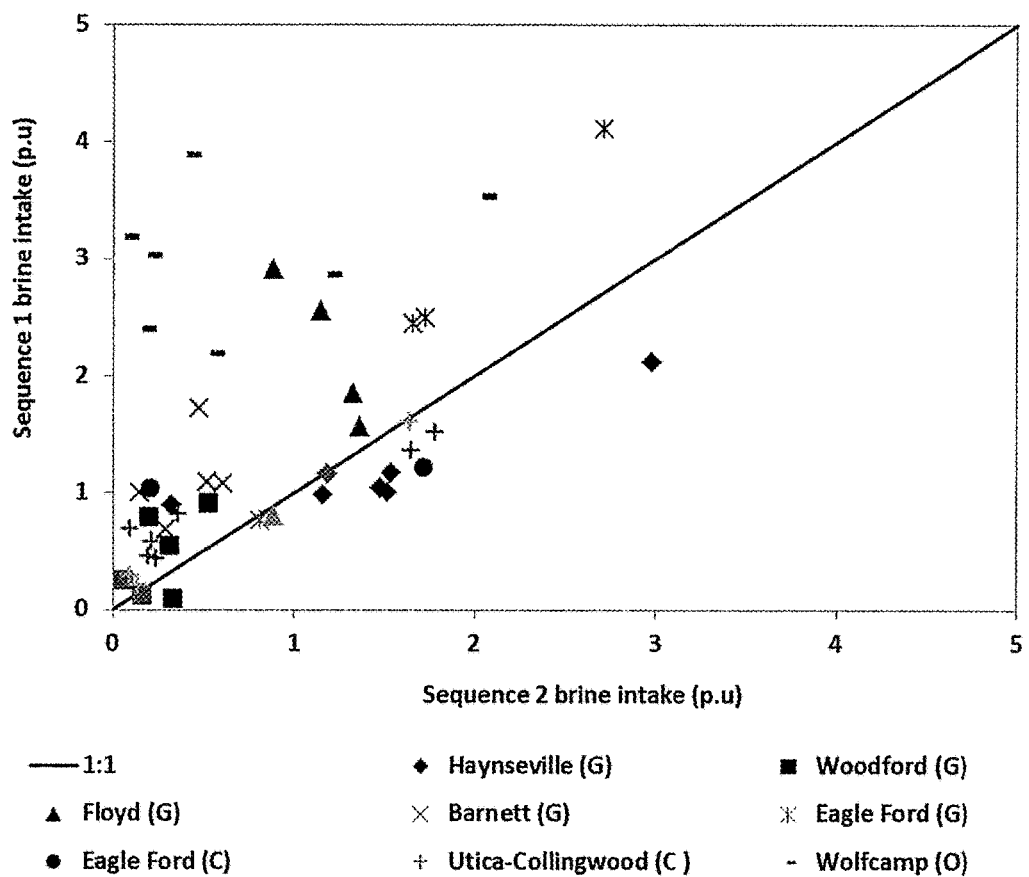
FIG. 2 is a comparison between the amounts of brine imbibed during sequence 1 and sequence 2 treatments. For most samples, the amount of brine imbibed during Sequence 1 is larger than the amount imbibed during Sequence 2 in companion samples. The letters in parenthesis within the figure legends are used to indicate that the shale samples are from the gas window (G), the condensate window (C) and the oil window (O).
Figure 3:
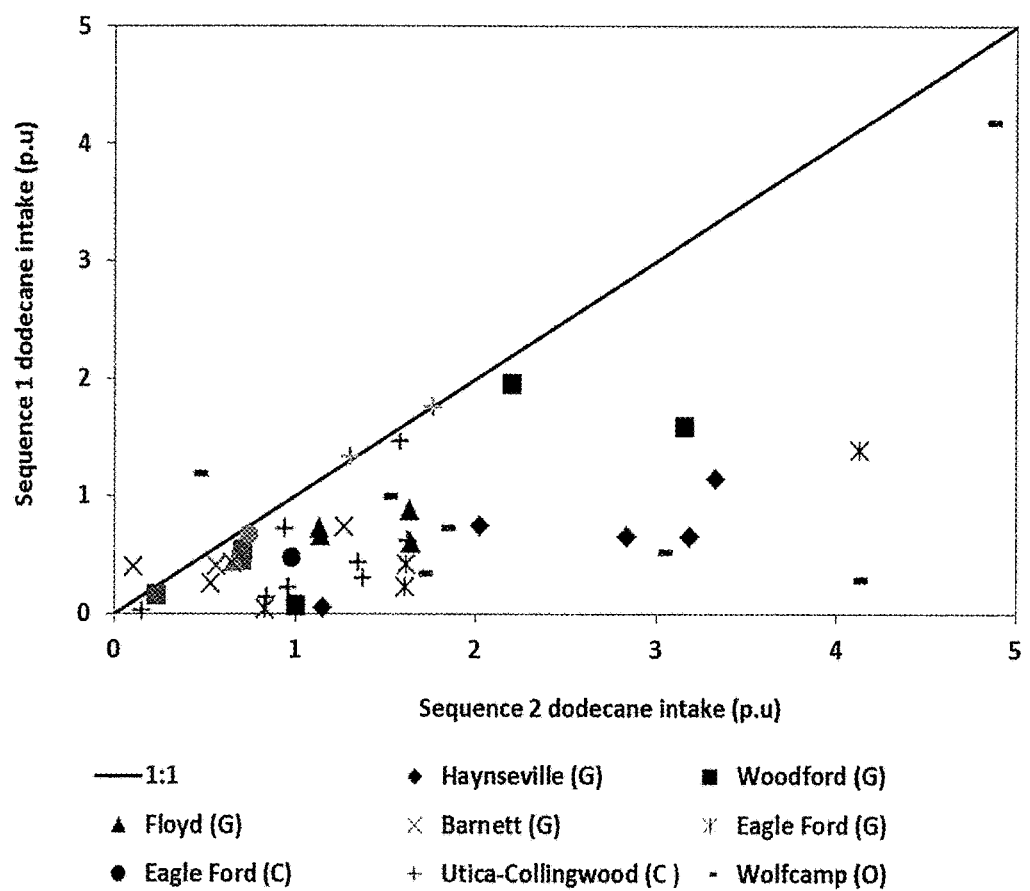
FIG. 3 is a comparison between the amounts of dodecane imbibed during Sequence 1 and Sequence 2 treatments in companion samples. In most samples, the amount of dodecane imbibed during Sequence 2 is larger than the amount imbibed during Sequence 1. The letters in parenthesis within the figure legends are used to indicate that the shale samples are from the gas window (G), the condensate window (C) and the oil window (O).

FIG. 1 shows the NMR $T_2$ spectra acquired for a Barnett sample during a Sequence 1 treatment. as well as the brine and dodecane intakes quantified by NMR FIG. 2 shows a comparison between the amounts of brine imbibed during Sequence 1 and Sequence 2 treatments, and FIG. 3 shows a comparison between the amounts of dodecane imbibed during Sequence 1 and Sequence 2 treatments. The letters in parenthesis within the figure legends are used to indicate that the shale samples are from the gas window (G), the condensate window (C) and the oil window (O).

If the water wet flow path is independent from the hydrocarbon wet flow path and vice versa, the amounts of brine imbibed during both sequences will be similar and the amount dodecane imbibed during both sequences will be the same. However, it was observed that the amount of brine imbibed during a Sequence 1 treatment is generally larger than the amount of brine imbibed during a Sequence 2 (FIG. 2). Conversely, the amount of dodecane imbibed during a Sequence 2 treatment is generally larger than the amount imbibed during a Sequence 1 treatment (FIG. 3).

These observations imply that the presence of brine reduces the accessibility of dodecane to some of the pores it could have accessed if brine was not present. Further, the presence of dodecane prevents brine from accessing some of the pores it can enter in the absence of dodecane. This phenomenon can only be observed if there are pores that are accessible by spontaneous imbibition to brine and dodecane. These pores are the mixed wettability pores. The fact that the imbibition of brine will affect the subsequent imbibition of dodecane, and vice versa also implies that most of the shale samples do not have a continuous connectivity of the water wet pores and hydrocarbon wet pores. The connectivity of either flow paths is enhanced by the presence of mixed wettability pores.

Figure 4:
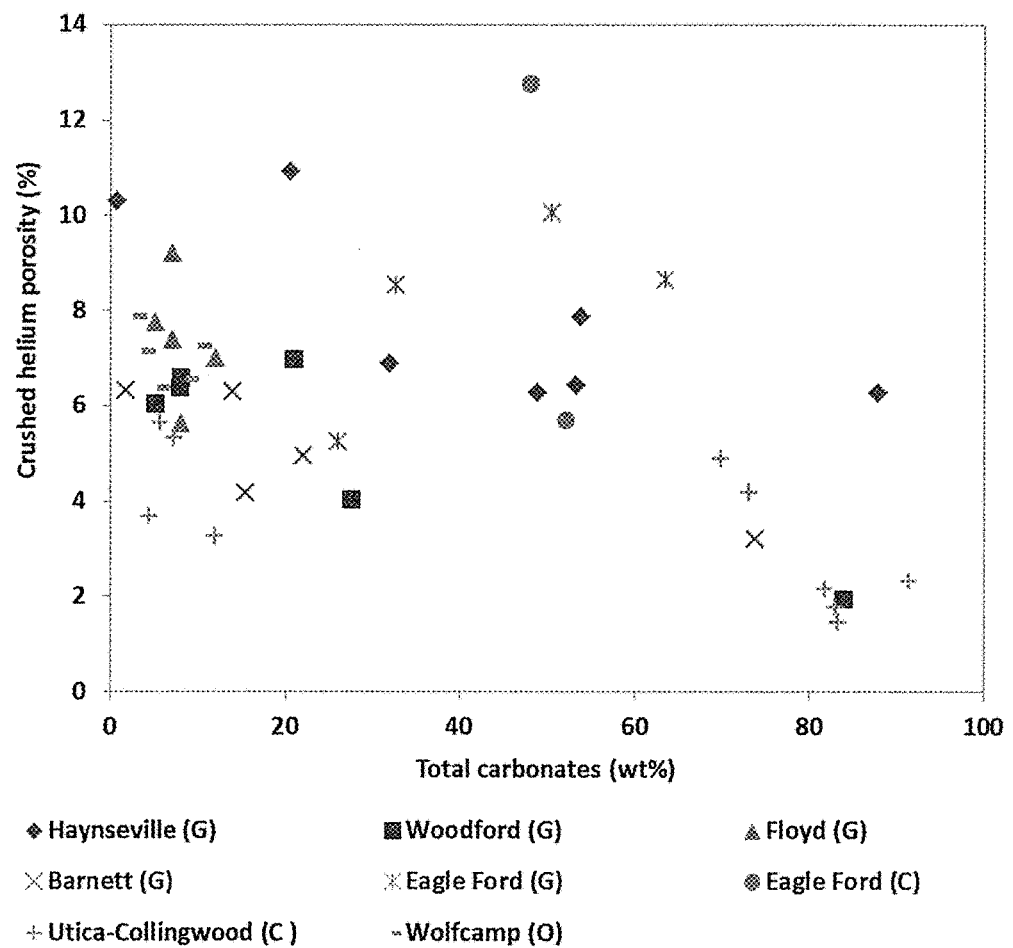
FIG. 4 shows crushed helium porosity as a function of the total carbonate content. A negative correlation is observed between porosity and carbonate content except for the Eagle Ford samples.

FIG. 4 shows a slight negative correlation between the crushed helium porosity and the carbonate content in all shale sample studied except the Eagle Ford samples. Therefore, the porosity associated with the carbonate minerals is generally negligible. This implies that the hydrocarbon wet porosity is essentially contained within the organic matter.

The organic content in all the samples studied was lower than 10 wt %. Considering an organic matter density of 1.4 g/cc and a shale bulk density of 2.4 g/cc, organic matter will represent a maximum of 18% of the sample volume; thus the organic matter will substantially be disseminated in connected or non-connected bodies throughout the shale samples. Therefore, during Sequence 1 treatment, brine will enter all the water wet pores, benefiting from the enhanced connectivity provided by the mixed wet pores; however, during Sequence 2 treatment, dodecane can only enter the connected hydrocarbon wet pores and the hydrocarbon wet pore accessible via the mixed wet pores. The hydrocarbon wet and mixed wettability pores accessible via water wet pores will not be accessible to dodecane by spontaneous imbibition.

To study the connectivity of the water wet pores, the mixed wet pores were blocked with dodecane. During Sequence 2 treatment, part of the mixed wet pores is occupied by dodecane. This will give the opportunity to evaluate the connectivity of the water wet pores. However, this connectivity will be affected by the amount of mixed wet pores accessible only through the water wet pores.

Figure 5:
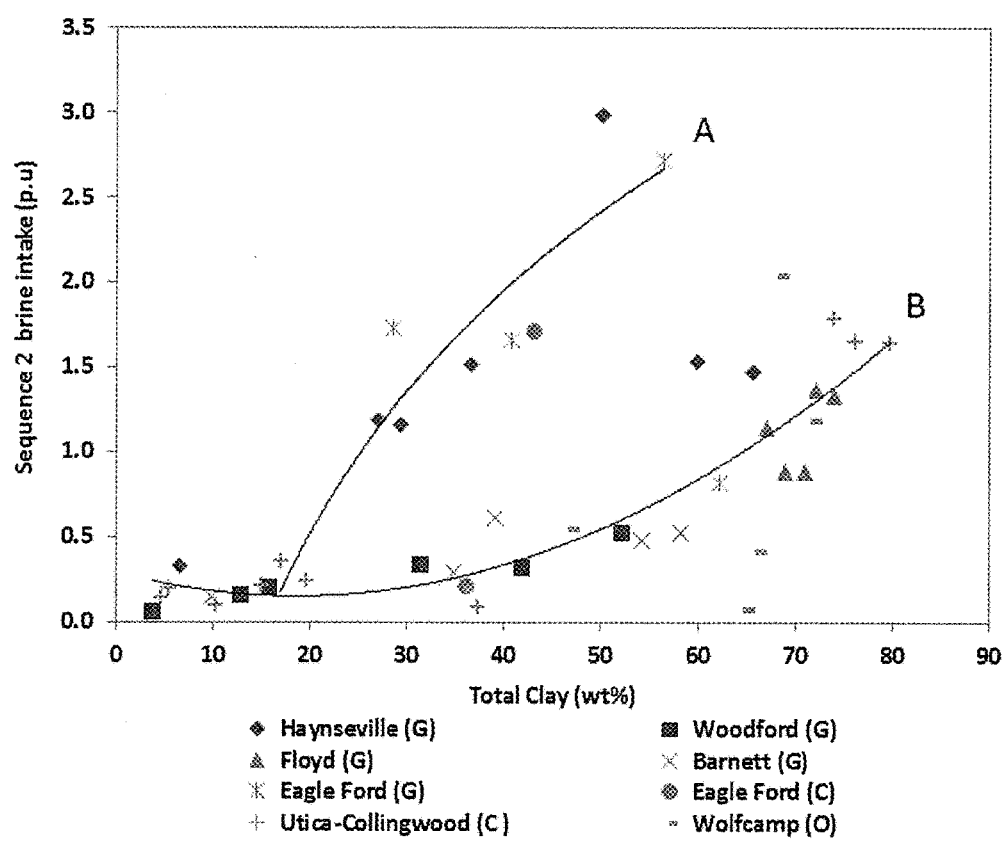
FIG. 5 is a graph showing a water wet pore connectivity template for several shale types based on an amount of brine imbibed during Sequence 2 as a function of the total clay content. Brine intake of a sample (measured as porosity units p.u.) is plotted against the Total Clay Content (measured as weight-percent) and the position on the figure determines the water wet pore connectivity level. 20 wt % of clays is necessary in order to develop a connected network of water wet pores.

FIG. 5 shows the amount of brine imbibed during Sequence 2 treatment as a function of the clay content. Below 20 wt % clay, the amount of brine imbibed is less than 0.5 p.u (porosity units) and does not show any correlation with the clay content, implying that the water wet pores are not connected beyond the edges of the samples. Above 20 wt % clay, the amount of brine imbibed exhibits a positive correlation with clay content. Therefore 20 wt % is the minimum amount of clay necessary in order to start the development of a connected water wet pore network. However, when the clay content is greater than 20 wt %, two trends are observed for the relationship between the amount of brine imbibed and the clay content.

The samples in trend A imbibed more brine than the samples in trend B for the same amount of clays. This observation implies that the samples in trend A have more mixed wet pores only accessible through the water wet pores.

Figure 6:
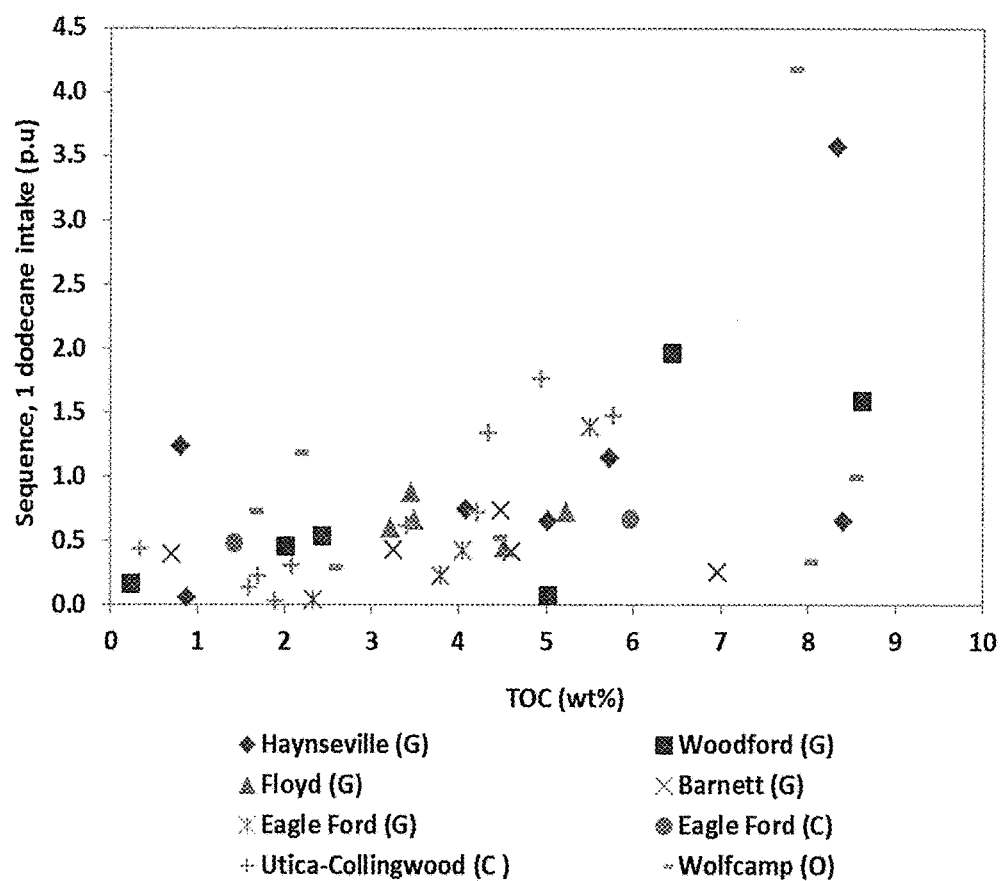
FIG. 6 is a graph showing a hydrocarbon wet pore connectivity template for several shale types, based on an amount of dodecane imbibed during Sequence 1 as a function of TOC (Total Organic Content). Dodecane intake of sample A (measured as porosity units p.u.) of the example is plotted against the TOC (measured as weight-percent) and the position on the figure determines the hydrocarbon wet pore connectivity level. This plot suggests that a minimum of 3 wt % of TOC is necessary in order to develop connectivity throughout the organic pores.

The connectivity of the hydrocarbon wet pore system was evaluated by plotting the amount of dodecane imbibed during a Sequence 1 treatment as function of TOC (FIG. 6). In this case, the water wet pores as well as the mixed wettability pores are occupied by brine. Below a TOC content of 3-4 wt % the amount of dodecane is generally less or equal to 0.5 p.u and does not show any correlation with TOC. Above 3-4 wt % TOC, an increase of the amount of dodecane was observed as a function of TOC implying that a minimum of 3-4 wt % TOC is necessary in order to develop a connected hydrocarbon wet pore network. The study of connectivity at atmospheric pressure with spontaneous imbibition data may not represent the connectivity during the production of hydrocarbon, because it does not include the hydrocarbon wet pores accessible only via water wet pores. Therefore the hydrocarbon wet pores connectivity was investigated as a function of fluids and pressure.

Pore Connectivity as a Function of Pressure

In order to evaluate pore connectivity as a function of pressure, 24 samples of shale were saturated with brine (25,000 ppm KCl) and dodecane. All saturations were conducted by applying a hydrostatic pressure of brine or dodecane. Companion samples from the same depths were used for the brine and dodecane saturation. The change in porosity due to saturation was monitored by acquiring the NMR $T_2$ distributions at TE=114 μsec with 2 MHz Oxford Geospec2™ instruments.

Figure 7:
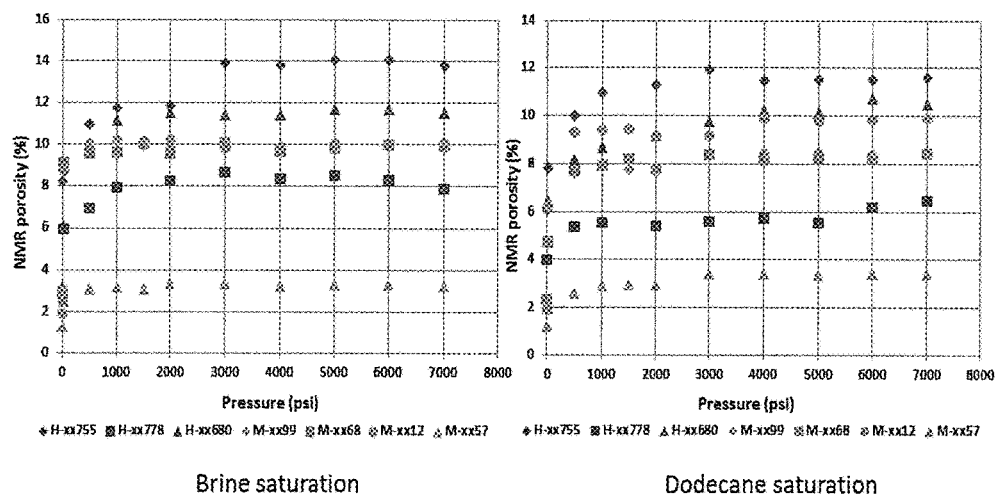
FIG. 7 is a graph showing change in percent porosity as measured by NMR plotted as a function of brine (left panel) or dodecane (right panel) saturation pressure. The majority of fluid intrusion occurs at pressures lower than 1000 psi. Most samples do not show porosity increase after 4000 psi of saturation pressure for both fluids.

To determine the pressure necessary to fully saturate the sample, a subset of samples were selected and their change in porosity was monitored as a function of saturation pressure (FIG. 7). The samples exhibited a rapid change in porosity, from simple spontaneous imbibition to a saturation pressure of 1000 psi. After a saturation pressure of 4000 psi, we observed a plateau in the change of porosity which would imply that the samples were fully saturated. We proceeded and saturated the rest of the samples at 7000 psi with brine and dodecane. At 7000 psi, brine and dodecane can enter respectively non-water wet and non-hydrocarbon wet pores with diameters as small as 4 nm.

Figure 8:
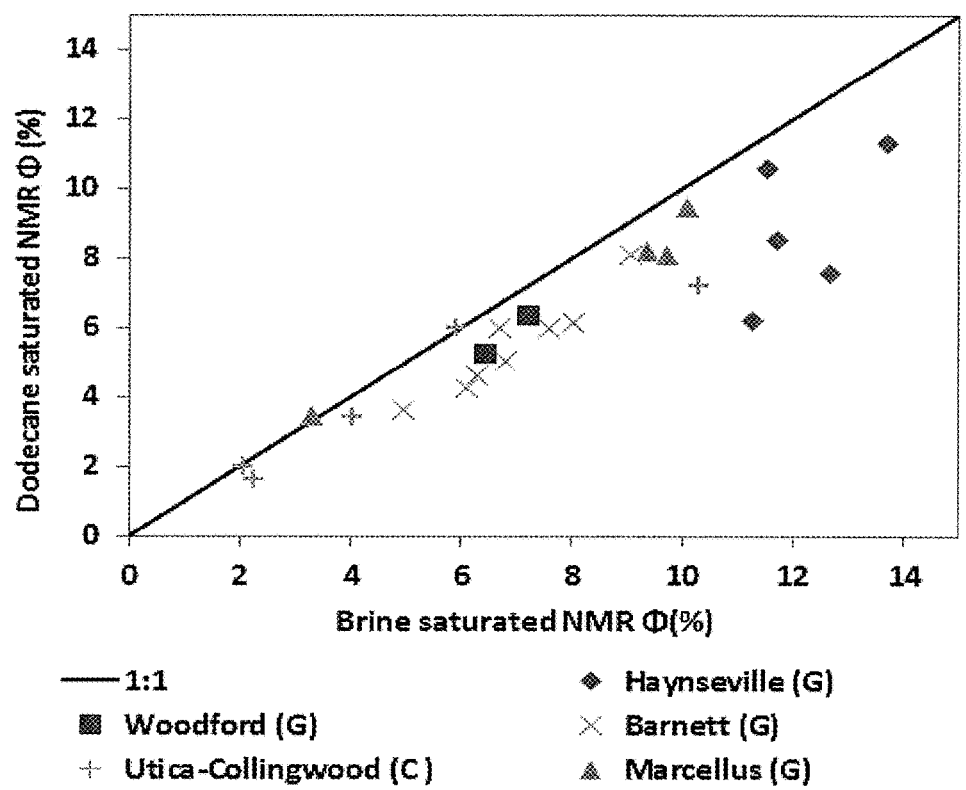
FIG. 8 shows a comparison between dodecane and brine saturated NMR porosity after saturation at 7000 psi. The brine saturated porosity is generally greater than the dodecane saturated porosity.

FIG. 8 illustrates the comparison between the brine and dodecane saturated porosity. In the majority of the cases, the brine saturated porosity is larger than the dodecane saturated porosity. The fact that brine porosity at 7000 psi is greater than dodecane porosity at 7000 psi implies that there is a fraction of the pore space that is accessible only through water wet pores with diameters smaller than 4 nm. However, the simple brine and dodecane porosity comparison cannot be used to determine if the majority of the pores accessible through water wet pores smaller than 4 nm are other water wet pores or hydrocarbon wet and/or mixed wet pores.

Figure 9:
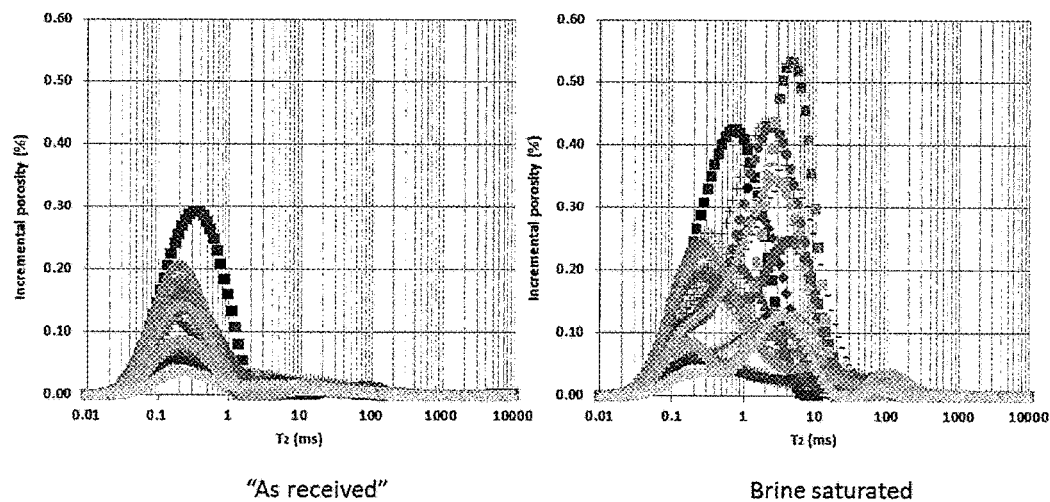
FIG. 9 shows NMR $T_2$ distributions of the "As received" samples and after brine saturation at 7000 psi. There is only one NMR $T_2$ peak in the "As received" samples, while two NMR $T_2$ peaks are generally observed for the brine saturated samples.
Figure 10:
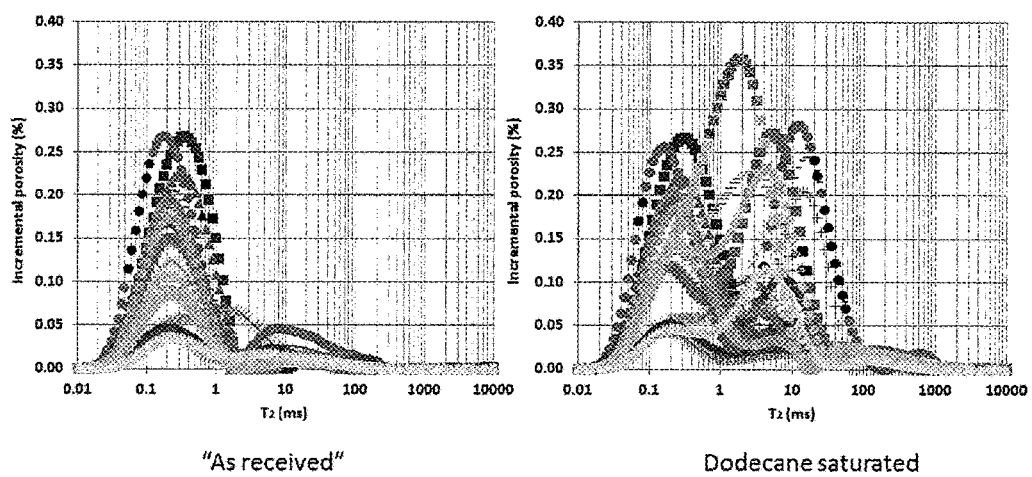
FIG. 10 shows NMR $T_2$ distributions of the "As received" samples and after dodecane saturation. While the "As received" samples have mainly one NMR $T_2$ peak, the dodecane saturated samples have bimodal NMR $T_2$ distributions.
Figure 11:
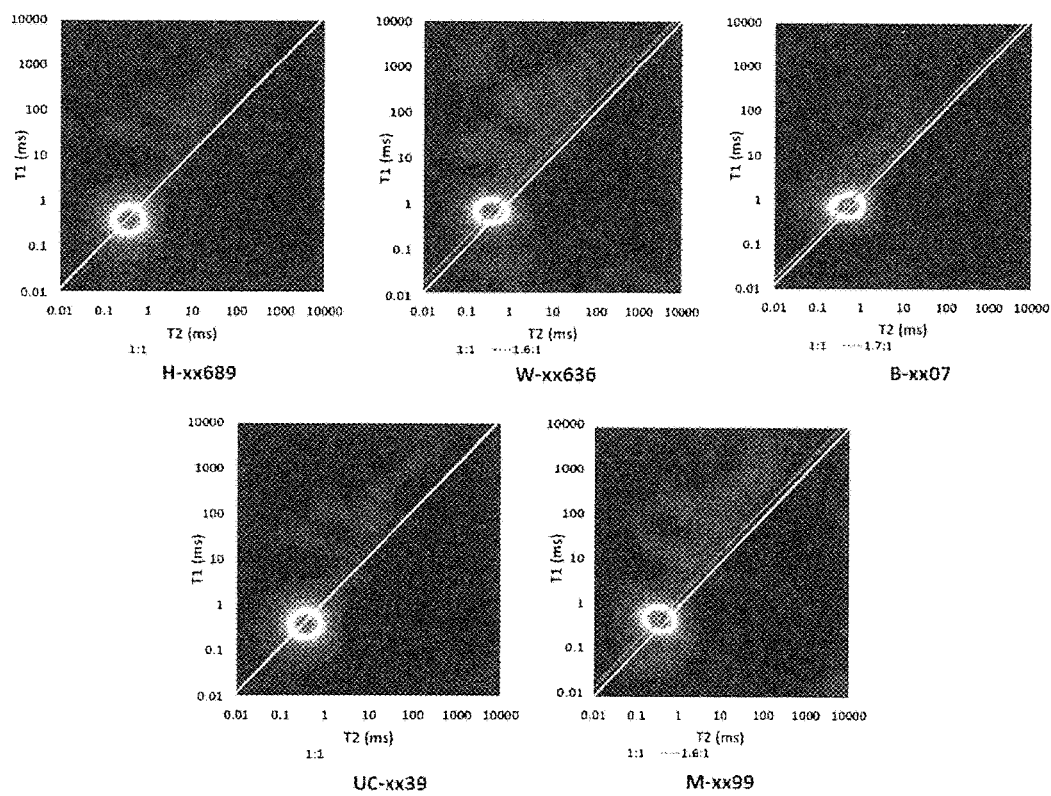
FIG. 11 shows T1-T2 maps of one "As received" sample from the Haynesville (H-xx689), Woodford (W-xx636), Barnett (B-xx07), Utica-Collingwood (UC-xx39), and Marcellus (M-xx99) shale formation. The maps show NMR signals with T1/T2 ratio between 1 and 1.7, which represent the residual brine.

In order to determine the wettability of those pores, we analyzed the NMR $T_2$ distributions of the "As received" samples as well as after brine and dodecane saturation at 7000 psi (FIG. 9 and FIG. 10, respectively). The "As received" NMR $T_2$ distributions show one NMR $T_2$ peak at $T_2$ times less than 1 ms representing the residual brine in the samples (FIG. 11).

Figure 12:
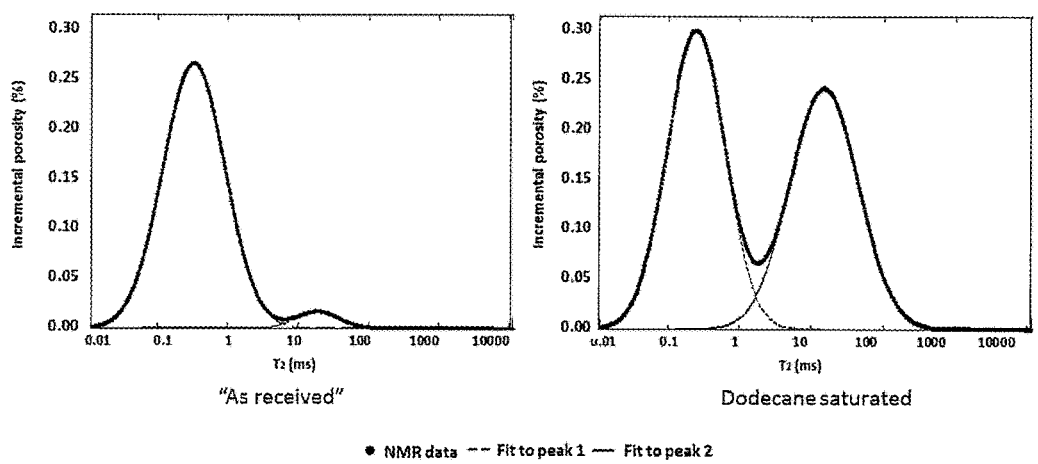
FIG. 12 is an example of Gaussian fitting applied to NMR $T_2$ distributions.

However, after dodecane and brine saturation, a bimodal distribution with a peak at $T_2$ times lower than 1 ms and another NMR $T_2$ peak between 7-20 ms was generally observed. This observation can be due to a bimodal pore size distribution, the presence of pores with two different surface relaxivities or the combination of both. The NMR $T_2$ distributions were fitted with Gaussian functions (FIG. 12). Peak 1 represents the NMR $T_2$ peak below 1 ms and peak 2, the NMR $T_2$ between 7-20 ms.

Figure 13:
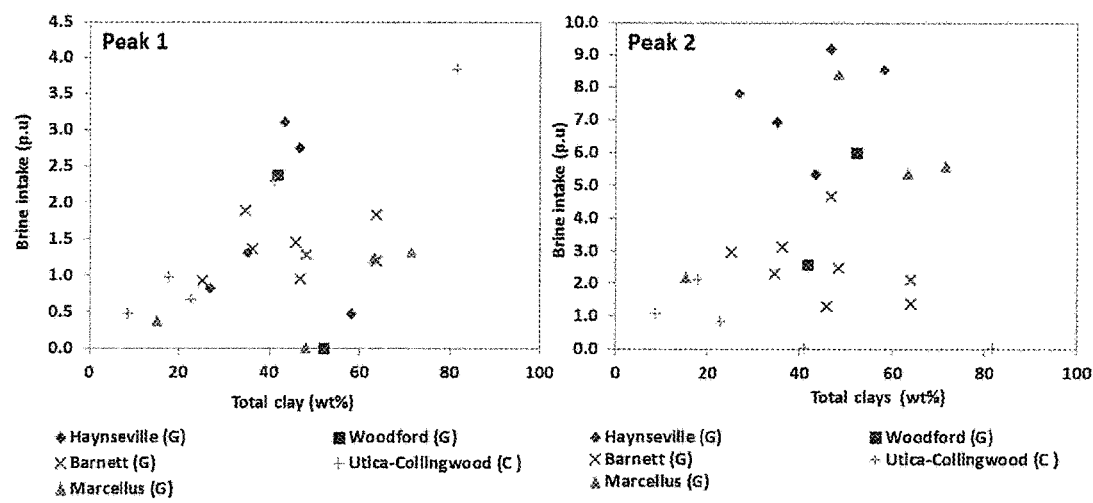
FIG. 13 shows brine intake of peak 1 and peak 2 after saturation at 7000 psi as a function of clay content. Note that the scales on the y axes are different. A positive correlation is observed between the increase of peak 1 and the clay content, but no relationship between the increase of peak 2 and the clay content.
Figure 14:
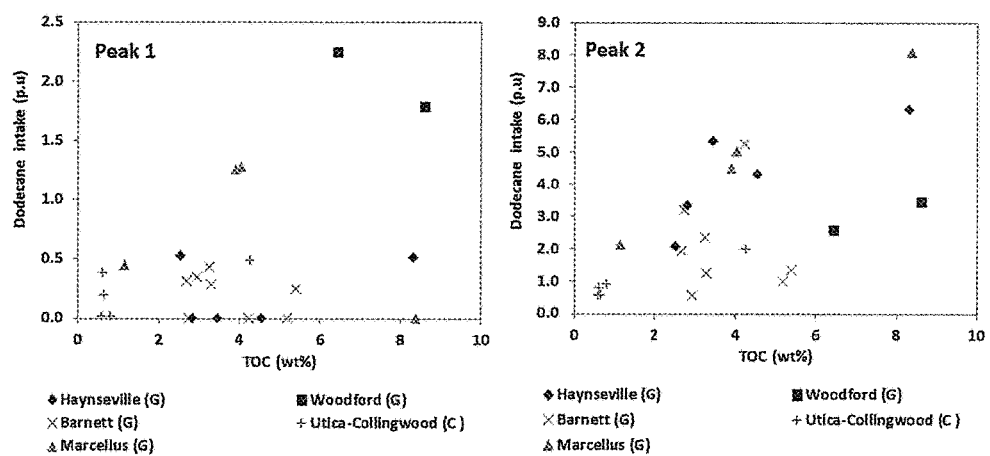
FIG. 14 shows dodecane intake of peak 1 and peak 2 after saturation at 7000 psi as function TOC. The scales on the y axes are different. In most samples the increase of peak 1 after dodecane saturation is less or equal to 0.5 p.u, and does not exhibit a correlation with TOC. However, the increase of peak 2 after dodecane saturation shows a positive correlation with TOC.

FIG. 13 illustrates the increase of peak 1 and 2 after brine saturation as a function of clay content. At clay content above 20 wt %, a continuous water wet flow path is developed. At TOC above 3 wt %, most of the organic bodies are connected; however, there are some organic that are only accessible through the water wet pores. FIG. 14 shows the dodecane intake in peak 1 and peak 2 as a function of TOC. A positive correlation was observed between the brine intake of peak 1 and clay content, and no relationship was observed between the brine intake of peak 2 and clay content. In most samples the dodecane intake of peak 1 is less than 0.5 p.u., and a relationship between the dodecane intake of peak 1 and TOC was not observed. The increase of peak 2 after dodecane saturation shows a positive correlation with TOC.

Figure 15:
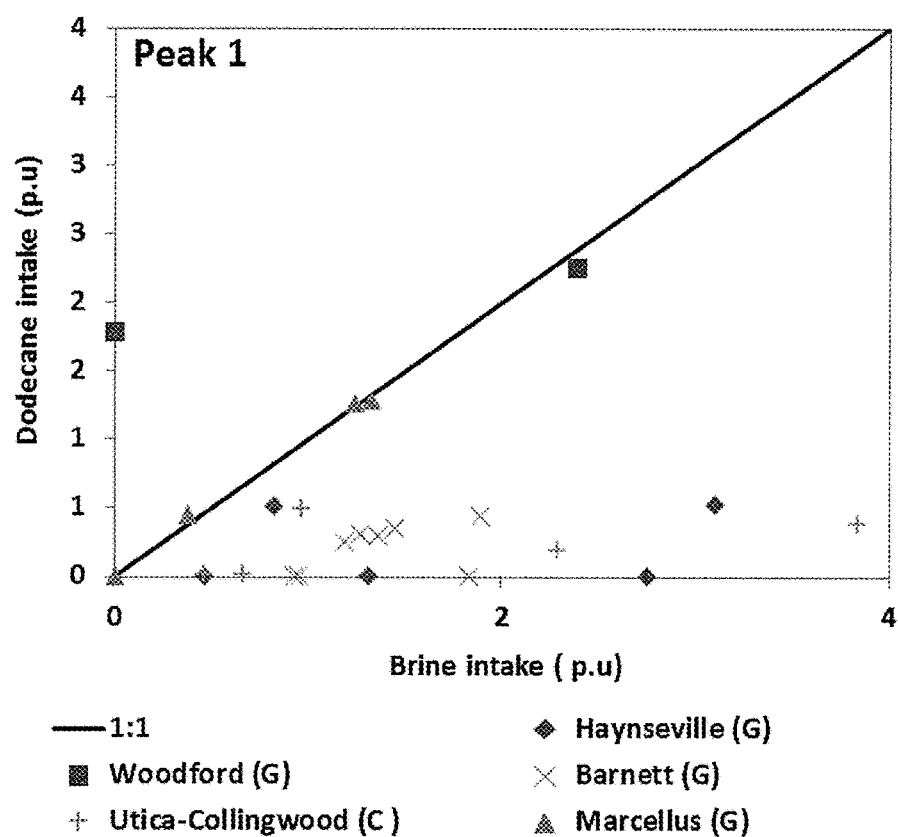
FIG. 15 shows a comparison between the dodecane intake of peak 1 and brine intake of peak 1 after saturation at 7000 psi. The brine intake is generally larger or equal to the dodecane intake.
Figure 16:
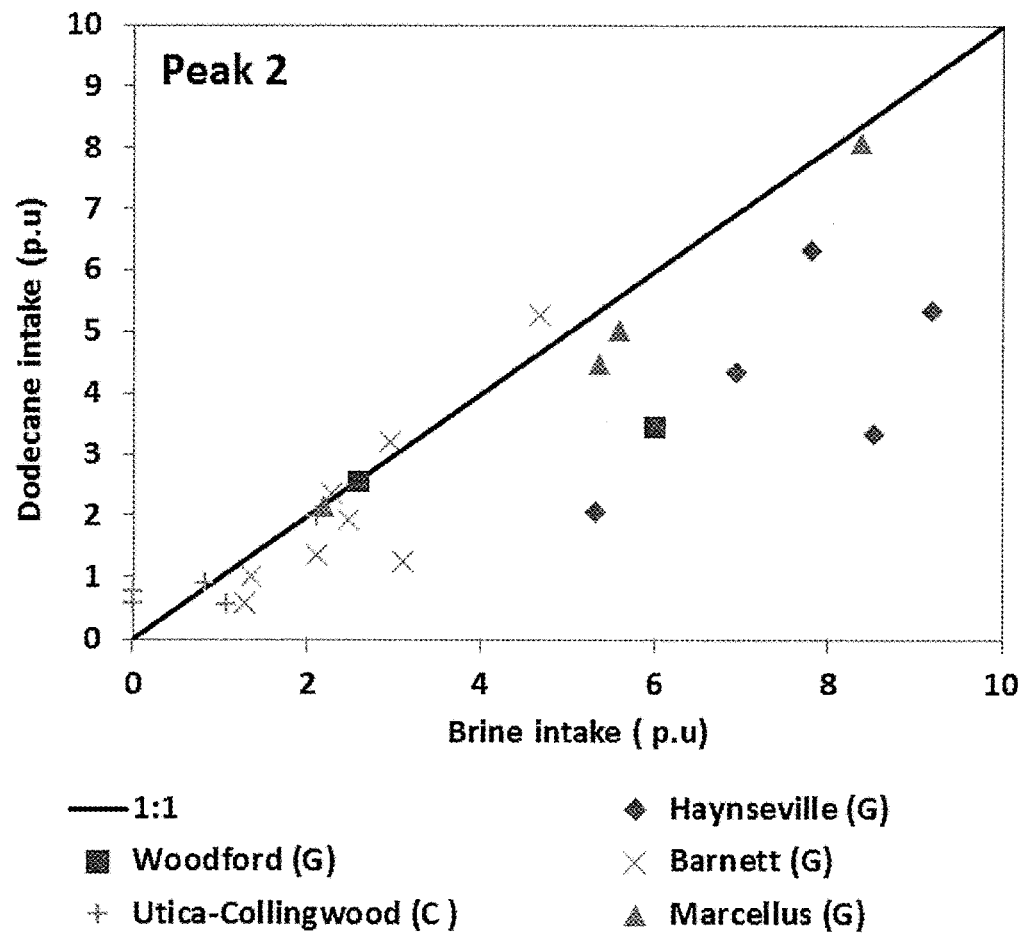
FIG. 16 shows a comparison between the dodecane intake of peak 2, and the brine intake of peak 2 after 7000 psi saturation. The dodecane intake of peak 2 is generally less or equal to the brine intake of peak 2.

These observations imply that pores associated with peak 1 are mainly comprised of water wet pores and the ones associated with peak 2 are essentially hydrocarbon wet pores. However, the scatter in the data indicate the presence of other types of pores such as mixed wet pores in peak 1 and peak 2. The brine intake of peak 1 is generally larger or equal to the dodecane intake of peak 1 (FIG. 15), and the dodecane intake of peak 2 is generally less or equal to the brine intake of peak 2 (FIG. 16). Therefore, the pore space that is accessible only through water wet pores with diameters smaller than 4 nm are water wet pores as well as hydrocarbon and mixed pores.

Figure 17:
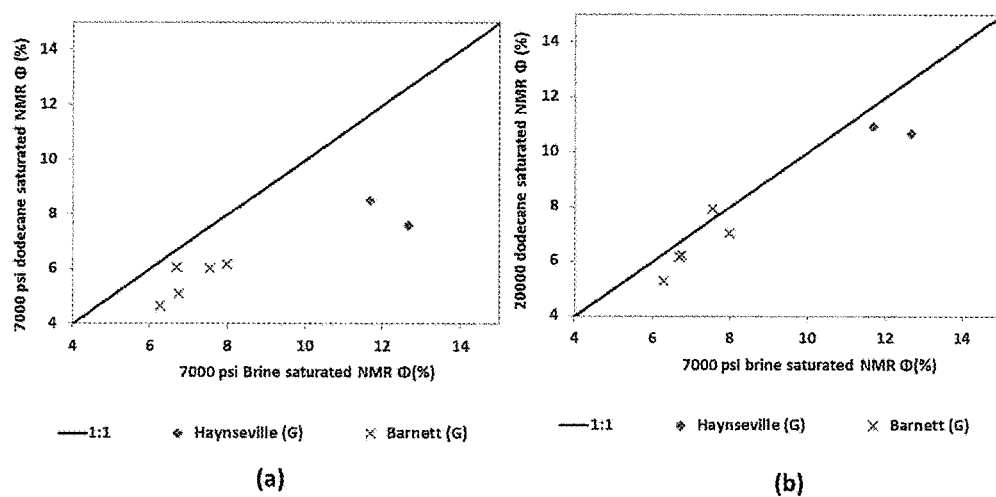
FIG. 17 shows a comparison between the porosity of a subset of samples saturated at 7000 psi with brine and dodecane (a) and at 20,000 psi with dodecane (b). The difference between the brine and dodecane porosity reduces after dodecane saturation at 20,000 psi.

In order to investigate the possibility of overcoming the barrier presented by the water wet pores with diameters smaller than 4 nm, a subset of samples was saturated at 20,000 psi with dodecane (FIG. 17). 20,000 psi of dodecane is equivalent to about 100,000 psi of mercury pressure. After saturation at 20,000 psi, the dodecane porosity increased, but was still slightly lower than the brine porosity.

Without wishing to be bound by theory, from a hydrocarbon storage and flow perspective, the results described herein indicate that hydrocarbon will be stored essentially in the hydrocarbon wet and mixed wettability pores but their deliverability will be hindered by the presence of water wet pores which will contain brine. The storage and flow of fluids as a function of pore wettability invalidates the concept of oil-water relative permeability in shales.

Figure 18:
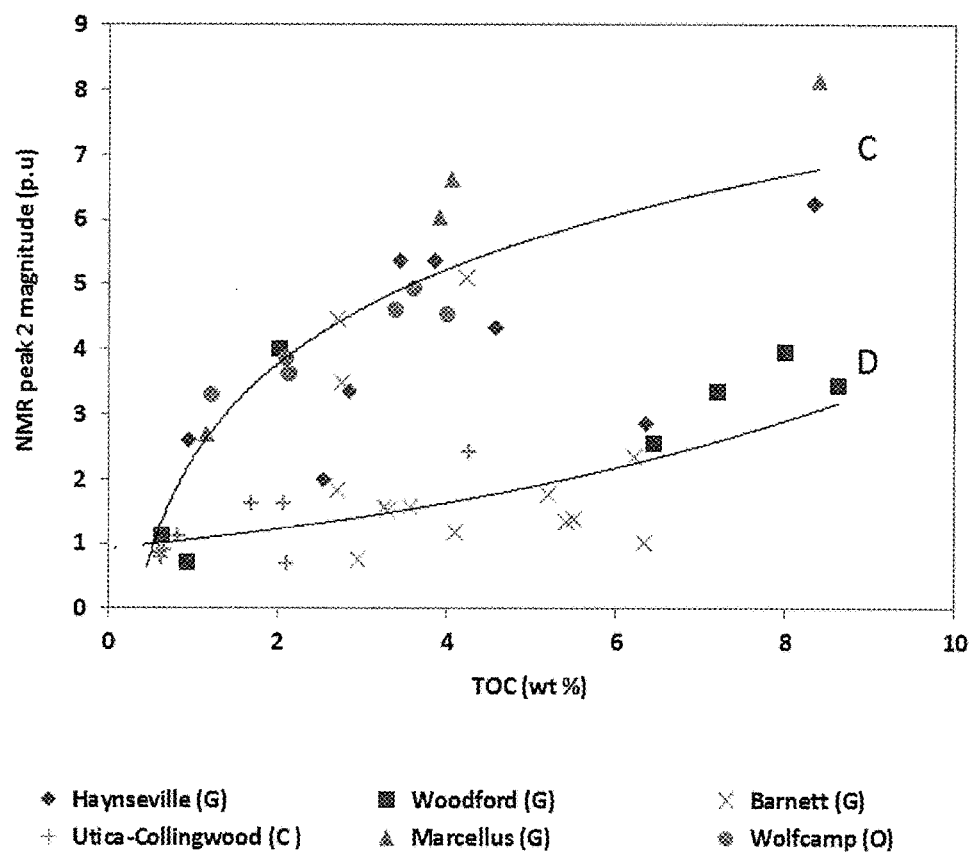
FIG. 18 shows the magnitude of peak 2 after dodecane saturation at 7000 psi as a function of TOC. Two trends (C and D) were observed. The samples in trend C have a higher proportion of water wet pores with diameters larger than 4 nm and or mixed wettability pores.

Peak 2 represents the hydrocarbon wet pores as well as some mixed wettability pores. Therefore the magnitude of peak 2 after dodecane saturation can be used as proxy for the amount of producible hydrocarbon at a given pore pressure. To further evaluate the productivity of hydrocarbon, another set of samples was saturated in addition to the 24 samples saturated with dodecane at 7000 psi. FIG. 18 illustrates the relationship between peak 2 for this extended dataset and TOC. There are two trends. The samples in trend C show a higher magnitude of peak 2 than the samples in trend D at the similar values of TOC. This behavior can be caused by the predominance of water wet pores with diameters larger than 4 nm in the population of water wet pores and or by the presence of more mixed wettability pores in the samples of trend C. Samples from all formations can be found in trend C or D. Therefore the main difference between shale formations is the ratio between the volume of facies with samples that belong to trend C or D. For a pore pressure of less than or equal to 7000 psi the facies represented by the samples in trend C will be better producers than those falling in trend D.

Unlike mercury intrusion-based methods for measuring pore connectivity, the presently disclosed methods do not require high pressure to induce fluid intrusion (e.g., see FIG. 7 which shows that the majority of fluid intrusion using the present method occurs at pressures lower than 1000 psi), and uses selective wetting fluids. The present method is thus non-compressive. In addition to the fact that it distinguishes the different wettability systems, the shale pore connectivity measurement method of the present disclosure is superior to measures of shale pore connectivity based on permeability measurements because it investigates the matrix properties of the rock and not the fractures.

The methods of the present disclosure will be more readily understood by reference to the following non-limiting example, which is included merely for purposes of illustration of certain aspects and embodiments of the present disclosure. The following detailed example is to be construed, as noted above, only as illustrative, and not as limiting of the disclosure in any way whatsoever. Those skilled in the art will promptly recognize appropriate variations from the various compositions, structures, components, procedures and methods. In certain embodiments, the following non-limiting experimental procedures are followed to determine the water wet pore and hydrocarbon wet pore network connectivity of a shale formation, as well as the porosity partitioning associated with these pore networks.

EXAMPLE

Figure 19:
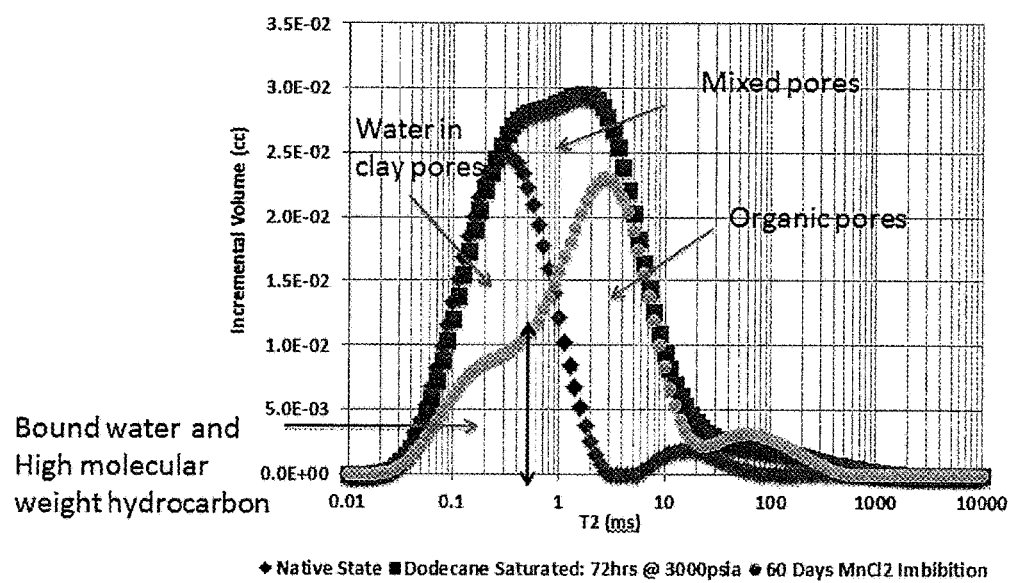
FIG. 19 is a graph of porosity partitioning obtained after dodecane displacement by $MnCl_2$ in sample C. Incremental volume (cc) is plotted against nuclear magnetic resonance (NMR) $T_2$ values measured in milliseconds (ms).

1. Select 3 solid samples from the same depth in the shale formation. For example, bulk volumes of the samples may be between 8 to 14 cc.
2. Measure Fourrier transform infrared spectroscopy (FTIR) mineralogy and total organic carbon (TOC) on one of the samples selected. The FTIR mineralogy should be measured after removal of organic matter by low temperature plasma ashing. TOC can be measured by any suitable method such as but not limited to the "LECO" method or Rock-Eval pyrolysis. TOC should be measured after removal of calcite by acidizing with a 10-15% HCl solution.
3. Label the three shale samples (e.g., with letters such as A, B, C).
4. Dry the samples until no weight change can be detected (e.g., at 100° C.).
5. Measure a pre-immersion NMR $T_2$ spectrum for each sample A, B, and C.
6. Immerse sample A in KCl brine (e.g., 25,000 ppm) for approximately 48 hours or more. In alternative, non-limiting, embodiments the duration of immersion can vary from 24 to 72 hours, or more.
7. Measure a post-brine immersion NMR $T_2$ spectrum of sample A after the KCl brine immersion step, then (within 2 minutes after the measurement of the NMR spectrum) immerse sample A in a single component light hydrocarbon (with viscosity lower than 3 cP, such as dodecane) for approximately 48 hours or more. In alternative, non-limiting, embodiments the duration of immersion can vary from 24 to 72 hours, or more.
8. Measure a post-hydrocarbon immersion NMR $T_2$ spectrum of sample A after immersion within the hydrocarbon.
9. Immerse samples B and C in a single component light hydrocarbon (with viscosity lower than 3 cP, such as dodecane) for approximately 48 hours or more. This step can be done before, or concurrently with, step 6. In alternative, non-limiting, embodiments the duration of immersion can vary from 24 to 72 hours, or more.
10. Measure post-hydrocarbon immersion NMR $T_2$ spectra of samples B and C after immersion within the hydrocarbon, then immerse (within 2 minutes after the measurement of the post-hydrocarbon immersion NMR spectrum) sample B in KCl brine (e.g., 25,000 ppm) for approximately 48 hours or more. In alternative, non-limiting, embodiments the duration of immersion can vary from 24 to 72 hours, or more.
11. Measure a post-brine immersion NMR $T_2$ spectrum of sample B after immersion within the KCl brine solution.
12. Saturate sample C (within about 24 hours after step 10) in a single component light hydrocarbon (with viscosity lower than 3 cP, such as dodecane) for approximately 48 hours or more at increasing pressure steps (e.g., at least 15 logarithmically spaced pressure steps between 50 and 7000 psi) until no hydrocarbon intake is observed, measuring a hydrocarbon saturation NMR $T_2$ spectrum of sample C after each stepwise increase in pressure. In alternative, non-limiting, embodiments the duration of immersion can vary from 24 to 72 hours, or more. NMR $T_2$ data is taken after every each step of increasing pressure.
13. Immerse sample C (within 24 hours after step 12) in an aqueous solution of $MnCl_2$ (e.g., 65%) or in an aqueous solution of $CuSO_4$ with no observable NMR signal.
14. Measure the NMR $T_2$ data of sample C (immersed within the $MnCl_2$ or $CuSO_4$ solution) until no change is observed in the NMR $T_2$ signal.
15. To determine the pore connectivity level of the organic (hydrocarbon wet), the NMR data acquired for sample A are plotted on the pore connectivity template of FIG. 6.
16. To determine the pore connectivity level of the inorganic (water wet) pores, the NMR data acquired for sample B are plotted on the pore connectivity template of FIG. 5.
17. A measurement of porosity partitioning can be obtained from the data acquired for sample C, by considering the displacement of the hydrocarbon (e.g., dodecane) from inorganic pores by the solution of $MnCl_2$ or $CuSO_4$ (FIG. 19).

In accordance with the foregoing, the present disclosure is directed, in at least some embodiments, to the following:

Clause 1. A method of estimating pore connectivity in a shale formation, comprising:
treating a first shale sample from the shale formation by (1) immersing the first shale sample in a brine solution for a first predetermined duration, and measuring a first NMR $T_2$ spectrum of the first shale sample after immersion in the brine solution, and (2) immersing the first shale sample in a liquid hydrocarbon for a second predetermined duration, and measuring a second NMR $T_2$ spectrum of the first shale sample after immersion in the liquid hydrocarbon;
treating a second shale sample from the shale formation by (1) immersing the second shale sample in the liquid hydrocarbon for a third predetermined duration, and measuring a first NMR $T_2$ spectrum of the second shale sample after immersion in the liquid hydrocarbon, and (2) immersing the second shale sample in the brine solution for a fourth predetermined duration, and measuring a second NMR $T_2$ spectrum of the second shale sample after immersion in the brine solution; and
estimating (1) an organic pore connectivity of the shale formation by evaluating the first NMR $T_2$ spectrum of the first shale sample and the second NMR $T_2$ spectrum of the first shale sample, and (2) an inorganic pore connectivity of the shale formation by evaluating the first NMR $T_2$ spectrum of the second shale sample, and the second NMR $T_2$ spectrum of the second shale sample.

Clause 2. The method of clause 1, further comprising:
treating a third shale sample from the shale formation by (1) immersing the third shale sample in the liquid hydrocarbon for a fifth predetermined duration, and measuring a first NMR $T_2$ spectrum of the third shale sample after immersion with the liquid hydrocarbon, (2) saturating the third shale sample in the liquid hydrocarbon under a protocol of stepwise pressure increases until further intake of liquid hydrocarbon ceases, and measuring a plurality of NMR $T_2$ spectra of the third shale sample following each stepwise pressure increase, then (3) immersing the third shale sample in an aqueous solution of $MnCl_2$ or $CuSO_4$, and measuring NMR $T_2$ data of the third shale sample immersed in the aqueous solution of $MnCl_2$ or $CuSO_4$ until substantially no change is observed in the NMR $T_2$ signal thereof, and obtaining a measurement of porosity partitioning of the shale formation by evaluating the first NMR $T_2$ spectrum of the third shale sample, the plurality of NMR $T_2$ spectra of the third shale sample following each stepwise pressure increase, and the NMR $T_2$ data of the third shale sample during immersion in the aqueous solution of $MnCl_2$ or $CuSO_4$.

Clause 3. The method of clause 1 or 2, wherein the estimate of organic pore connectivity of the shale formation by evaluating the first NMR $T_2$ spectrum of the first shale sample and the second NMR $T_2$ spectrum of the first shale sample is made in reference to a template based on total organic content plotted against hydrocarbon intake.

Clause 4. The method of any one of clauses 1-3, wherein the estimate of inorganic pore connectivity of the shale formation by evaluating the first NMR $T_2$ spectrum of the second shale sample and the second NMR $T_2$ spectrum of the second shale sample is made in reference to a template based on total clay content plotted against brine intake.

Clause 5. The method of clause 2, wherein the measurement of porosity partitioning of the shale formation by evaluating the first NMR $T_2$ spectrum of the third shale sample, the plurality of NMR $T_2$ spectra of the third shale sample, and the NMR $T_2$ data of the third shale sample is made in reference to a template based on $T_2$ relaxation time incremental volume.

Clause 6. The method of any one of clauses 1-5, wherein the first predetermined duration is at least about 48 hours.

Clause 7. The method of any one of clauses 1-6, wherein the second predetermined duration is at least about 48 hours.

Clause 8. The method of any one of clauses 1-7, wherein the third predetermined duration is at least about 48 hours.

Clause 9. The method of any one of clauses 1-8, wherein the fourth predetermined duration is at least about 48 hours.

Clause 10. The method of any one of clauses 1-9, wherein the fifth predetermined duration is at least about 48 hours.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. A method of estimating pore connectivity in a shale formation, comprising:
    treating a first shale sample from the shale formation by:
        immersing the first shale sample in a brine solution for a first predetermined duration, and measuring a first NMR $T_2$ spectrum of the first shale sample after immersion in the brine solution, wherein the first NMR $T_2$ spectrum of the first shale sample is obtained by subtracting an echo-train of the first shale sample in an as received state from an echo-train of the first shale sample in a first brine imbibed state thereby obtaining a first brine echo-train after subtraction, and inverting the first brine echo-train after subtraction, and
        immersing the first shale sample in a liquid hydrocarbon for a second predetermined duration, and measuring a second NMR $T_2$ SPECTRUM OF THE FIRST SHALE SAMPLE AFTER IMMERSION in the liquid hydrocarbon, wherein the second NMR $T_2$ spectrum of the first shale sample is obtained by subtracting the echo-train of the first shale sample in the first brine imbibed state from an echo-train of the first shale sample in a liquid hydrocarbon imbibed state thereby obtaining a first liquid hydrocarbon echo-train after subtraction, and inverting the first liquid hydrocarbon echo-train after subtraction;
    treating a second shale sample from the shale formation by:
        immersing the second shale sample in the liquid hydrocarbon for a third predetermined duration, and measuring a first NMR $T_2$ spectrum of the second shale sample after immersion in the liquid hydrocarbon, wherein the first NMR $T_2$ spectrum of the second shale sample is obtained by subtracting an echo-train of the second shale sample in an as received state from an echo-train of the second shale sample in a liquid hydrocarbon imbibed state thereby obtaining a second liquid hydrocarbon echo-train after subtraction, and inverting the second liquid hydrocarbon echo-train after subtraction; and
        immersing the second shale sample in the brine solution for a fourth predetermined duration, and measuring a second NMR $T_2$ spectrum of the second shale sample after immersion in the brine solution, wherein the second NMR $T_2$ spectrum of the second shale sample is obtained by subtracting the echo-train of the second shale sample in the liquid hydrocarbon imbibed state from an echo-train of the second shale sample in a second brine imbibed state thereby obtaining a second brine echo-train after subtraction, and inverting the second brine echo-train after subtraction, and
    estimating (1) an organic pore connectivity of the shale formation by evaluating the first NMR $T_2$ spectrum of the first shale sample and the second NMR $T_2$ spectrum of the first shale sample in reference to a template based on total organic content of the first shale sample plotted against hydrocarbon intake of the first shale sample, and (2) an inorganic pore connectivity of the shale formation by evaluating the first NMR $T_2$ spectrum of the second shale sample, and the second NMR $T_2$ spectrum of the second shale sample in reference to a template based on total clay content of the second shale sample plotted against brine intake of the second shale sample.

2. The method of claim 1 further comprising treating a third shale sample from the shale formation by:

immersing the third shale sample in the liquid hydrocarbon for a fifth predetermined duration, and measuring a first NMR $T_2$ spectrum of the third shale sample after immersion with the liquid hydrocarbon by obtaining an echo-train from the third shale sample after immersion, saturating the third shale sample in the liquid hydrocarbon under a protocol of stepwise pressure increases until further intake of liquid hydrocarbon ceases, and measuring a plurality of NMR $T_2$ spectra of the third shale sample following each stepwise pressure increase by obtaining an echo-train from the third shale sample after each stepwise pressure increase, then immersing the third shale sample in an aqueous solution of $MnCl_2$ or $CuSO_4$, and measuring NMR $T_2$ data of the third shale sample immersed in the aqueous solution of $MnCl_2$ or $CuSO_4$ by obtaining an echo-train from the third shale sample after immersion in the aqueous sample until substantially no change is observed in the NMR $T_2$ signal thereof, and obtaining a measurement of porosity partitioning of the shale formation by evaluating the first NMR $T_2$ spectrum of the third shale sample, the plurality of NMR $T_2$ spectra of the third shale sample following each stepwise pressure increase, and the NMR $T_2$ data of the third shale sample during immersion in the aqueous solution of $MnCl_2$ or $CuSO_4$ in reference to a template based on incremental volume plotted against $T_2$ relaxation time.

3. The method of claim 2, wherein the fifth predetermined duration is at least about 48 hours.

4. The method of claim 1, wherein the first predetermined duration is at least about 48 hours.

5. The method of claim 1, wherein the second predetermined duration is at least about 48 hours.

6. The method of claim 1, wherein the third predetermined duration is at least about 48 hours.

7. The method of claim 1, wherein the fourth predetermined duration is at least about 48 hours.

* * * * *